(12) United States Patent
Huh

(10) Patent No.: US 7,971,267 B2
(45) Date of Patent: Jul. 5, 2011

(54) AIR SUPPLYING DEVICE FOR WELDING MASK

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 811 days.

(21) Appl. No.: 12/032,275

(22) Filed: Feb. 15, 2008

(65) Prior Publication Data

US 2009/0089908 A1 Apr. 9, 2009

(30) Foreign Application Priority Data

Oct. 9, 2007 (KR) .................. 10-2007-0101353

(51) Int. Cl.
*A61F 9/06* (2006.01)
(52) U.S. Cl. ........................................................ 2/8.6
(58) Field of Classification Search ... 2/8.6; 128/201.24
See application file for complete search history.

(56) References Cited

U.S. PATENT DOCUMENTS

| | | | | |
|---|---|---|---|---|
| 4,227,520 A * | 10/1980 | Lord | | 128/201.24 |
| 5,533,500 A * | 7/1996 | Her-Mou | | 128/201.25 |
| 5,887,281 A * | 3/1999 | Green et al. | | 2/171.3 |
| 7,178,932 B1 * | 2/2007 | Buckman | | 362/105 |
| 2009/0055987 A1 * | 3/2009 | Becker et al. | | 2/8.6 |

OTHER PUBLICATIONS

U.S. Appl. No. 29/279,174, filed Apr. 23, 2007 for the applicant, Moon Young Huh.

* cited by examiner

*Primary Examiner* — Katherine Moran
(74) *Attorney, Agent, or Firm* — Cantor Colburn LLP

(57) ABSTRACT

Disclosed is an air supplying device for a welding mask, capable of supplying clean air into a face shield of the welding mask. According to an embodiment of the present invention, more specifically, the air supplying device comprises a housing connected to the face shield, a connection member connected to a supply port of the housing, a first opening/closing member connected to a first outlet part of the housing, and a second opening/closing member connected to a second outlet of the housing. Therefore, the air supplying device is capable of conveniently adjusting direction of a bellows hose connected to supply the air and also adjusting quantity and direction of the air being supplied.

8 Claims, 5 Drawing Sheets

AIR SUPPLYING DEVICE FOR WELDING MASK

BACKGROUND OF THE INVENTION

1. Field of the Invention

The present invention relates to a welding mask, and more particularly to an air supplying device for a welding mask, capable of supplying clean air into the welding mask for an operator wearing the welding mask, while conveniently adjusting direction of a bellows hose connected to supply the air and also adjusting quantity and direction of the air being supplied.

2. Description of the Related Art

In general, welding work not only generates lots of sparks but may even harm an operator because the sparks of parent metal being welded may spout to the operator's face due to sudden ultrahigh heat and resistance. Furthermore, since smoke generated by the welding work contains various toxic substances, the smoke could do great harm to the operator when being inhaled. Accordingly, a welding mask has been needed and used to prevent inhalation of the smoke as well as protecting the operator's sight and face.

The welding mask generally comprises a head band that helps wearing of the welding mask on the operator's head, and a face shield axially connected with both sides of the head band to shield the operator's face. Additionally, a viewing window is provided on a front of the face shield to enable the operator to see the front therethrough while protecting the operator's eyes from the strong welding sparks.

Such a welding mask has been developed in various configurations according to the use. Especially, the development has been made concerning the technology not only for protecting the operator from the smoke by supplying clean air into the welding mask but also enabling the operator to perform the welding being favorably supplied with the clean air even in a hermetic space or a high-temperature space.

SUMMARY OF THE INVENTION

Therefore, the present invention has been made in view of the above problems, and it is an object of the present invention to provide an air supplying device for a welding mask, capable of solving problems of a conventional air supplying device which limits free movement of the operator's head owing to a fixed bellows hose connected to supply the air and also highly limits drawing up of the face shield.

It is another object of the present invention to provide an air supplying device for a welding mask, capable of solving conventional inconveniences in adjusting position, quantity or direction of the air supply.

In accordance with the present invention, the above and other objects can be accomplished by the provision of an air supplying device for a welding mask which comprises a head band that helps wearing of the welding mask on an operator's head and a face shield axially connected with both sides of the head band and having a viewing window provided on a front thereof, to supply air from a rear end of the face shield into the face shield, the air supplying device comprising a housing connected to an inside of the face shield, thereby forming a hermetic space for circulating the air therethrough, and comprised of a supply port formed at a middle rear end thereof to guide in the air, a first outlet part formed at a middle front end of the housing in the form of a curved surface to exhaust the air over the viewing window, and a second outlet formed on each side of the front end and extended respectively toward both sides of the viewing window to exhaust the air therethrough, a connection member axially connected to the supply port to be pivotable laterally by a predetermined angle and also connected to a bellows hose for supplying the air at a rear end thereof; a first opening/closing member connected to the first outlet part to interrupt and allow the air supply; and second opening/closing members connected to the both second outlets respectively to interrupt and allow the air supply.

Here, the supply port of the housing may have a tunnel form opened forward and backward and include a rotational shaft mounted to a bottom thereof. The connection member may be fitted with the supply port and includes curved surfaces on lateral sides thereof to closely contact with lateral surfaces of the supply port during the pivoting as fitted in the supply port and a connection piece formed at a lower part thereof to be rotatably connected to the rotational shaft.

The first outlet part may comprise front and rear first outlets disposed respectively on front and rear positions of the curved surface thereof, the front first outlet to exhaust the air to a front of the operator's face and the rear first outlet to exhaust the air above the operator's forehead, with a slit formed in a forward and backward direction in the middle of the first outlet part, and the first opening/closing member is formed as a curved surface for close contact with an inside of the first outlet in axial connection with the first outlet and extended at front and rear ends thereof by a length for blocking any one or both of the front and rear first outlets, and includes vent holes formed on the curved surface corresponding to the front and rear first outlets and a dial formed in the middle of the vent holes to be protruded out through the slit to rotate the first opening/closing member.

A guide projection may be formed at an inner end of each second outlet and a guide recess is formed at both sides of each second opening/closing member to receive the guide projection so that the second opening/closing member hingedly opens and closes the second outlet.

The air supplying device may further comprise a cover that covers a top of the housing protruded from the rear end of the face shield.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Hereinafter, an exemplary embodiment of the present invention will be described in detail with reference to the accompanying drawings.

Figure 1:
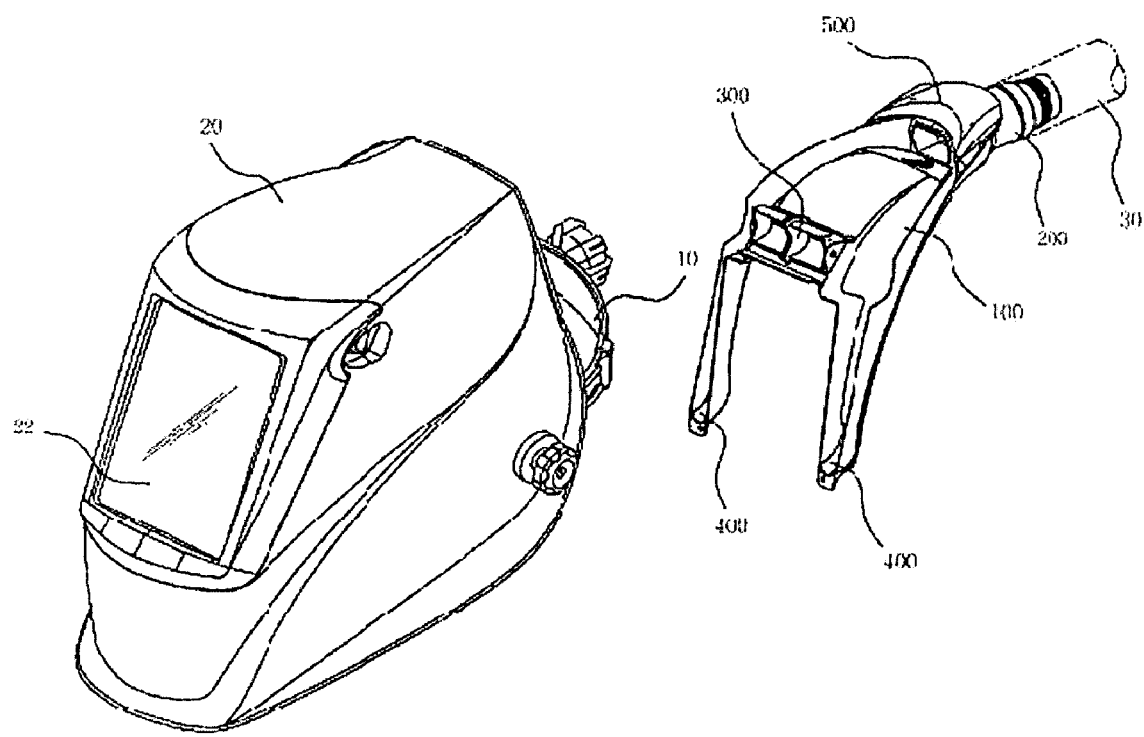
FIG. 1 is a perspective view of an air supplying device for a welding mask, according to an embodiment of the present invention, as separated from the welding mask.
Figure 2:
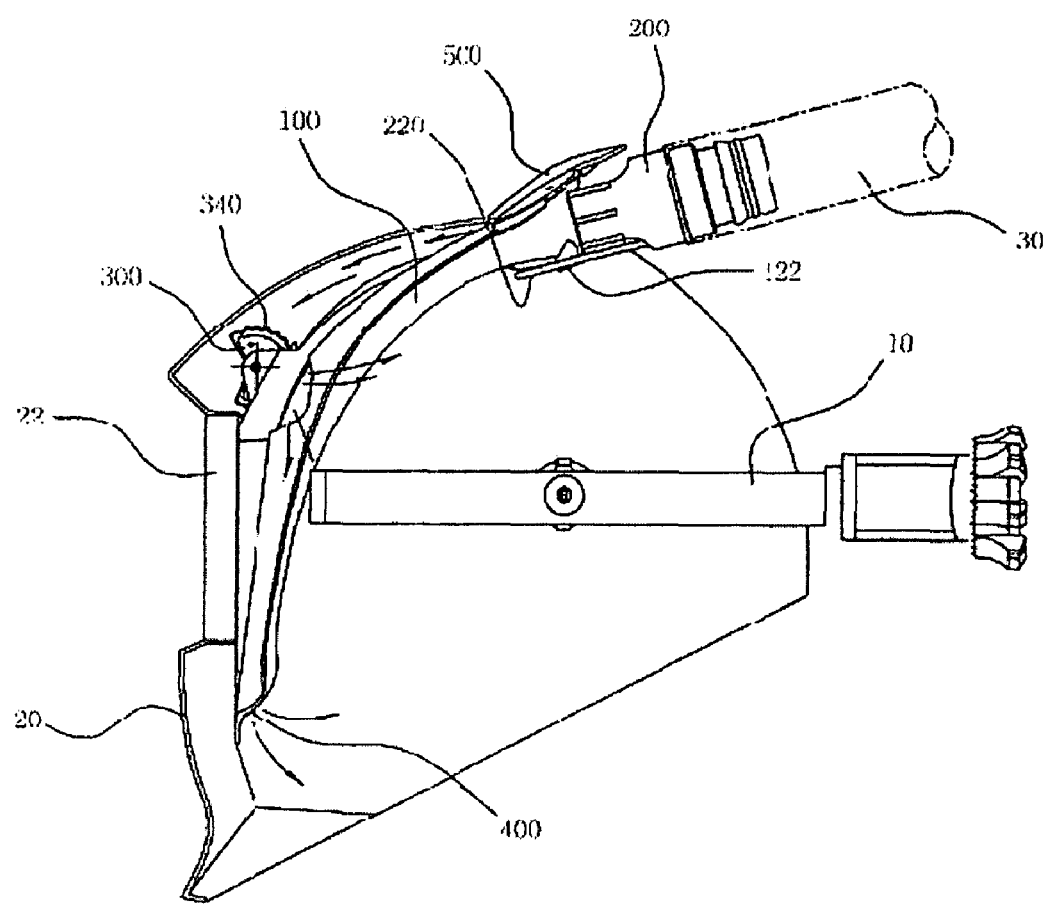
FIG. 2 is a sectional view of the air supplying device according to the embodiment of the present invention, as assembled.
Figure 3:
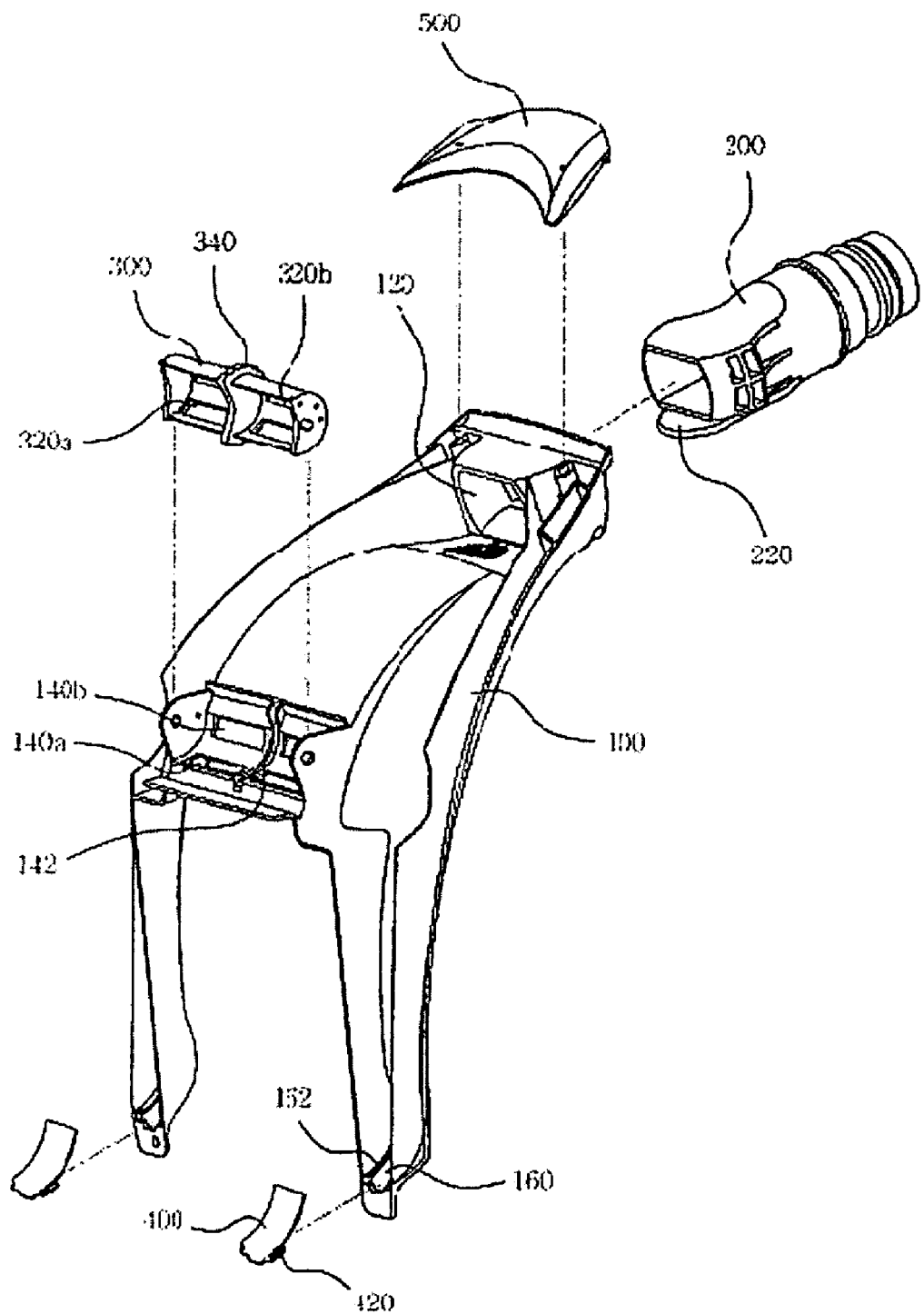
FIG. 3 is an exploded perspective view showing main elements of the air supplying device according to the embodiment of the present invention.
Figure 4:
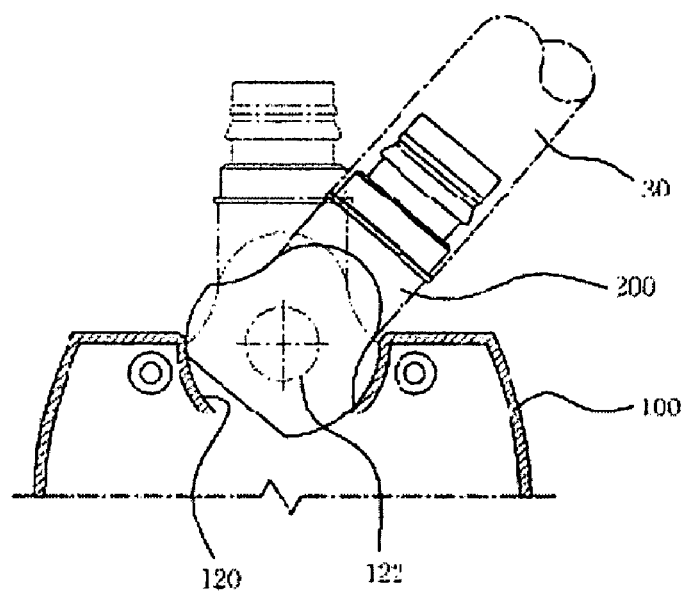
FIG. 4 is an operational view of a connection member of the air supplying device according to the embodiment of the present invention.
Figure 5:
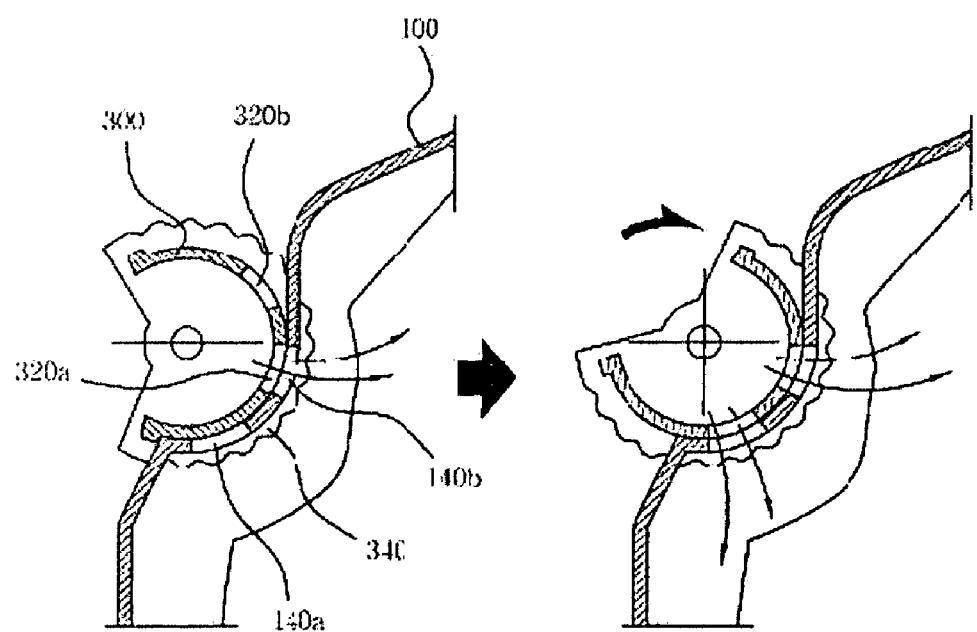
FIG. 5 is an operational view of a first opening/closing member of the air supplying device according to the embodiment of the present invention.
Figure 6:
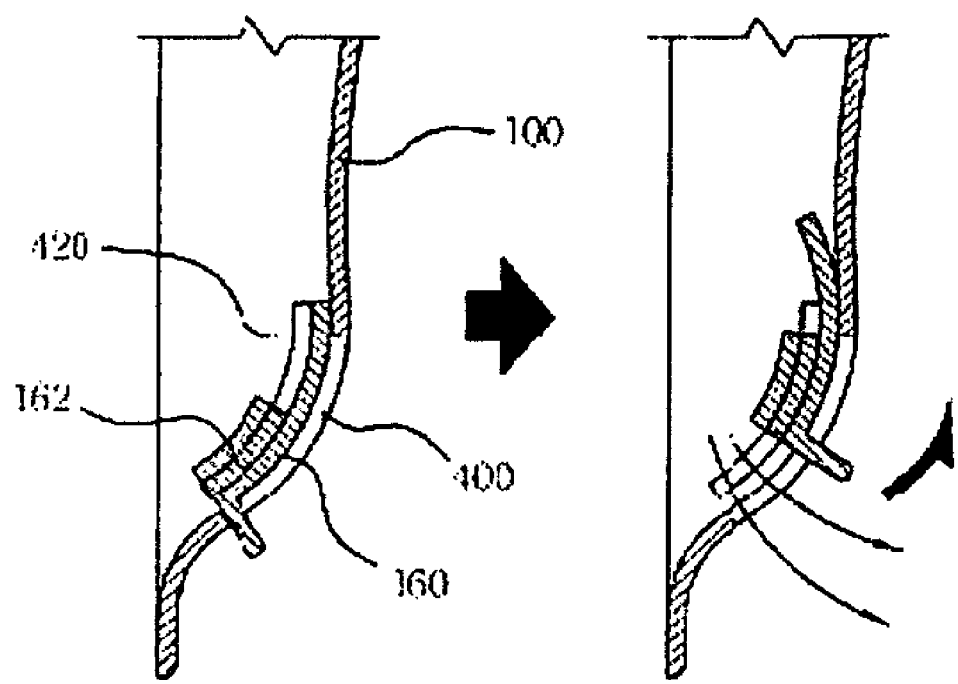
FIG. 6 is an operational view of a second opening/closing member of the air supplying device according to the embodiment of the present invention.

FIG. 1 is a perspective view of an air supplying device for a welding mask, according to an embodiment of the present invention, as separated from the welding mask, FIG. 2 is a sectional view of the air supplying device as assembled, FIG. 3 is an exploded perspective view showing main elements of the air supplying device, FIG. 4 is an operational view of a connection member of the air supplying device, FIG. 5 is an operational view of a first opening/closing member of the air supplying device, and FIG. 6 is an operational view of a second opening/closing member of the air supplying device.

Referring to FIG. 1 through FIG. 6, the air supplying device for a welding mask mainly comprises a housing 100 connected to a face shield 20 which includes a viewing window 22, a connection member 200 axially connected to a supply port 120 of the housing 100, a first opening/closing member 300 connected to a first outlet part formed at the housing 100, and a second opening/closing member 400 connected to a second outlet of the housing 100.

The housing 100 is connected to an inside of the face shield 20, thereby forming a hermetic space for circulating air therethrough, and structured to supply clean air toward an operator's face. More particularly, a supply port 120 is formed at a middle rear end of the housing 100 to guide in the air. The first outlet part is formed at a middle front end of the housing 100 in the form of a curved surface to exhaust the air through an upper part of the viewing window 22. In addition, a second outlet 160 is formed on each side of the front end of the housing 100 and extended respectively toward both sides of the viewing window 22 to exhaust the air therethrough.

As described above, the housing 100 according to the embodiment of the present invention has the structure capable of supplying the air to the operator's face evenly through the upper side and the lower side thereof.

The supply port 120 is in the form of a tunnel opened forward and backward. A rotational shaft 122 is formed on a bottom of the supply port 120. Therefore, the supply port 120 supports the connection member 200 by upper and lower ends thereof so that rotation of the air supplying device can be stably performed. As shown in the drawings, a top cover 500 may be further provided at the upper part of the supply port 120 in order to hermetically cover an exposed space of the housing 100, including the supply port 120 exposed to the rear end of the face shield 20.

The first outlet part comprises front and rear first outlets 140a and 140b which are disposed respectively on front and rear positions of the curved surface thereof. More specifically, the front first outlet 140a exhausts the air to the front of the operator's face while the rear first outlet 140b exhausts the air above the operator's forehead. Here, the front and rear first outlets 140a and 140b each comprise a pair of holes arranged laterally. A slit 142 cut in a forward and backward direction is formed between the respective pairs of the front and rear first outlets 140a and 140b, that is, in the middle of the first outlet part. The slit 142 is formed to expose a dial 340 of the first opening/closing member 300 therethrough so that the first opening/closing member 300 can be rotated by the operator.

In addition, a guide projection 162 is formed on an inner end of the second outlet 160 so that the second outlet 160 as opened downward can be opened and closed by the second opening/closing member 400.

The connection member 200 is axially connected to the supply port 120 to be pivoted laterally by a predetermined angle. A bellows hose 30 is connected to a rear end of the connection member 200. The connection member 200 is fitted into the supply port 120, and includes curved surfaces on lateral sides thereof to be in close contact with lateral surfaces of the supply port 120 during the pivoting as fitted in the supply port 120. In addition, a connection piece 220 is formed at a lower part of the connection member 200 to be rotatably connected to the rotational shaft 122 of the supply port 120. Here, the connection piece 220 is spaced apart from the lower part of the connection member 200 that is inserted in the supply port 120, so as to be inserted under a lower surface of the supply port 120.

According to the above structure, as shown in FIG. 4, supply of the air can be performed favorably while the connection member 200 connected to the supply port 120 rotates by the predetermined angle. Furthermore, during this, leakage of the air can be prevented because the lateral sides of the supply port 120 and the connection member 200 are closely contacting each other.

The first opening/closing member 300 interrupts and allows the supply of the air in connection with the first outlets 140a and 140b. More specifically, the first opening/closing member 300 is formed as a curved surface for close contact with the inside of the first outlet part as axially connected with the first outlet part. Also, vent holes 320a and 320b are formed on the curved surface of the first opening/closing member 300, corresponding to the front and rear first outlets 140a and 140b respectively. Front and rear ends of first opening/closing member 300 are extended by a length for blocking any one or both of the front and rear first outlets 140a and 140b. In the middle of the vent holes 320a and 320b, the dial 340 for rotating the first opening/closing member 300 is formed to be protruded out through the slit 142.

In other words, the first opening/closing member 300 has a cylindrical shape partially cut out in a longitudinal direction. As the first opening/closing member 300 is axially connected with the first outlets 140a and 140b, the operator is capable of opening and closing the first opening/closing member 300 by rotating the dial 340 as shown in FIG. 5. Here, the first outlets 140a and 140b disposed at the front and the rear respectively can be opened and closed selectively, that is, both opened, either opened or both closed, in accordance with a rotational direction of the first opening/closing member 300. In a state where the front and rear first outlets 140a and 140b are all closed by the first opening/closing member 300, exhaust of the air is performed through only the second outlet 160 at the lower part.

The second opening/closing member 400 is connected with the both second outlets 160 to interrupt and allow the air supply. On both sides of each second opening member 400, a guide recess 420 is formed corresponding to the guide projection 162 of the second outlet 160, such that the second connection member 400 can be opened or closed as necessary as shown in FIG. 6. Referring to the drawings, the second outlet 160 and the second opening/closing member 400 may be formed as a curved surface.

According to the above-described structure, the supply port 120 of the housing 100 and the bellows hose 300 which supplies the air to the supply port 120 through the connection member 200 can be pivoted laterally relative to each other. Therefore, the operator wearing the welding mask is capable of moving more freely. In addition, by the association between the first and second outlets 140a, 140b and 160 and the first and second opening/closing members 300 and 400, position, quantity and direction of the air supply can be adjusted as the operator wishes. Thus, the convenience in use is improved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An air supplying device in combination with a welding mask the mask comprising a head band that helps wearing of the welding mask on an operator's head and a face shield axially connected with both sides of the head band and having a viewing window provided on a front thereof, to supply air from a rear end of the face shield into the face shield, the air supplying device comprising:

a housing connected to an inside of the face shield, thereby forming a hermetic space for circulating the air therethrough, and comprised of a supply port formed at a middle rear end thereof to guide in the air, a first outlet part formed at a middle front end in the form of a curved surface to exhaust the air over the viewing window, and a second outlet formed on each side of the front end and extended respectively toward both sides of the viewing window to exhaust the air therethrough, a connection member axially connected to the supply port to be pivotable laterally by a predetermined angle and also connected to a bellows hose for supplying the air at a rear end thereof;

a first opening/closing member connected to the first outlet part to interrupt and allow the air supply; and second opening/closing members connected to the both second outlets respectively to interrupt and allow the air supply.

2. The air supplying device according to claim 1, wherein the supply port of the housing has a tunnel form opened forward and backward and includes a rotational shaft mounted to a bottom thereof, and the connection member is fitted with the supply port and includes curved surfaces on lateral sides thereof to closely contact with lateral surfaces of the supply port during the pivoting as fitted in the supply port and a connection piece formed at a lower part thereof to be rotatably connected to the rotational shaft.

3. The air supplying device according to claim 1, wherein the first outlet part comprises front and rear first outlets disposed respectively on front and rear positions of the curved surface thereof, the front first outlet to exhaust the air to a front of the operator's face and the rear first outlet to exhaust the air above the operator's forehead, with a slit formed in a forward and backward direction in the middle of the first outlet part, and the first opening/closing member is formed as a curved surface for close contact with an inside of the first outlet part in axial connection with the first outlet part and extended at front and rear ends thereof by a length for blocking any one or both of the front and rear first outlets, and includes vent holes formed on the curved surface corresponding to the front and rear first outlets and a dial formed in the middle of the vent holes to be protruded out through the slit to rotate the first opening/closing member.

4. The air supplying device according to claim 1, wherein a guide projection is formed at an inner end of each second outlet and a guide recess is formed at both sides of each second opening/closing member to receive the guide projection so that the second opening/closing member hingedly opens and closes the second outlet.

5. The air supplying device according to claim 1, further comprising a cover that covers a top of the housing protruded from the rear end of the face shield.

6. The air supplying device according to claim 2, wherein the first outlet part comprises front and rear first outlets disposed respectively on front and rear positions of the curved surface thereof, the front first outlet to exhaust the air to a front of the operator's face and the rear first outlet to exhaust the air above the operator's forehead, with a slit formed in a forward and backward direction in the middle of the first outlet part, and the first opening/closing member is formed as a curved surface for close contact with an inside of the first outlet part in axial connection with the first outlet part and extended at front and rear ends thereof by a length for blocking any one or both of the front and rear first outlets, and includes vent holes formed on the curved surface corresponding to the front and rear first outlets and a dial formed in the middle of the vent holes to be protruded out through the slit to rotate the first opening/closing member.

7. The air supplying device according to claim 2, wherein a guide projection is formed at an inner end of each second outlet and a guide recess is formed at both sides of each second opening/closing member to receive the guide projection so that the second opening/closing member hingedly opens and closes the second outlet.

8. The air supplying device according to claim 2, further comprising a cover that covers a top or the housing protruded from the rear end of the face shield.

* * * * *